US007160718B2

(12) United States Patent
Levoguer et al.

(10) Patent No.: US 7,160,718 B2

(45) Date of Patent: Jan. 9, 2007

(54) CONTROLLED SAMPLE ENVIRONMENT FOR ANALYTICAL DEVICES

(75) Inventors: Carl Levoguer, Reading (GB); Daryl R Williams, Slough (GB); Dylan H Simpson, Ruislip (GB)

(73) Assignee: Surface Measurement Systems Limited, London (GB)

( * ) Notice: Subject to any disclaimer, the term of this patent is extended or adjusted under 35 U.S.C. 154(b) by 562 days.

(21) Appl. No.: 10/296,720

(22) PCT Filed: May 30, 2001

(86) PCT No.: PCT/GB01/02403

§ 371 (c)(1),
(2), (4) Date: Nov. 26, 2002

(87) PCT Pub. No.: WO01/92460

PCT Pub. Date: Dec. 6, 2001

(65) Prior Publication Data

US 2003/0143721 A1 Jul. 31, 2003

(51) Int. Cl.
*C12M 1/36* (2006.01)

(52) U.S. Cl. ............................... 435/286.6; 435/288.7; 422/82.05; 422/99; 250/576; 378/73

(58) Field of Classification Search ..................... None
See application file for complete search history.

(56) References Cited

U.S. PATENT DOCUMENTS

| | | | |
|---|---|---|---|
| 4,301,252 | A | 11/1981 | Baker et al. |
| 4,336,329 | A | 6/1982 | Hesse et al. |
| 4,707,086 | A | 11/1987 | Dahan et al. |
| 5,083,558 | A | 1/1992 | Thomas et al. |
| 5,257,128 | A | 10/1993 | Diller et al. |

FOREIGN PATENT DOCUMENTS

| | | |
|---|---|---|
| DE | 94 14 990 U | 11/1994 |
| WO | WO 00/25129 | 5/2000 |

OTHER PUBLICATIONS

International Search Report, Aug. 10, 2001.

*Primary Examiner*—David Redding
(74) *Attorney, Agent, or Firm*—Pillsbury Winthrop Shaw Pittman LLC

(57) ABSTRACT

Apparatus for examining a sample by microscopy, spectroscopy or crystallography under controlled environmental conditions. The apparatus comprises a sample chamber (1) which is fed by a gas stream (19) having a known vapor content, which is generated by mixing two gas streams (18 & 16), one substantially saturated in a volatile substance (18) and one substantially free of the volatile substance (16), in a controlled manner. The temperature of the apparatus, and particularly of the sample chamber (1), is accurately controlled and regulated by temperature controller (7).

20 Claims, 2 Drawing Sheets

CONTROLLED SAMPLE ENVIRONMENT FOR ANALYTICAL DEVICES

This application is the National Phase of International Application PCT/GB01/02403, filed May 30, 2001, which designated the U.S. and claimed priority to Great Britain Application No. 0013261.3 filed May 31, 2000.

The present invention relates to apparatus for providing a controlled sample environment for use in conjunction with a microscope, a photon spectroscopic device, an X-ray diffractometer or other analytical device.

Many analytical methods across a range of scientific disciplines are carried out with the sample in an atmosphere which may not be beneficial to the sample and lead to unreliable analytical results. A chemical might degrade in the presence of oxygen or water vapour in the atmosphere or a biological system, e.g. a cell culture, might require a specific environment in order to maintain its integrity. Chemical degradation or loss of integrity of a biological system is known to take place, in adverse conditions, over the course of an analytical experiment or between experiments which is disadvantageous where several sets of results are required.

Many organic and inorganic materials are known to react or change chemical and/or morphological states in the presence or absence of specific water vapour concentrations. Consequently, the correct characterisation of such materials must occur under precisely controlled environmental conditions. An analytical system where the environment is controlled in terms of temperature and atmosphere (or vapour content) is desirable. Chemists wishing to make real-time observations, e.g. by infra-red spectroscopy, of a chemical-reaction mediated by atmospheric composition such as air oxidation or hydrogenation under controlled conditions would benefit from such a system.

It is frequently desirable to observe biological cells, for a variety of purposes, for extended periods of time. Such experiments may include time lapse photography where the precise conditions applied to the system may be important, but with use of a normal microscope leads to degradation of the system or the requirement that the biological sample is returned, e.g. to an incubator, between observations. The problems faced here are even more pronounced for preparing video footage of a biological event through a suitably adapted microscope.

The provision of particular physical conditions for the optical microscope and other analytical methods has been sought as is evidenced by several of the following patents.

U.S. Pat. No. 4,301,252 relates to a biological incubator for use in conjunction with an optical microscope such that a controlled atmosphere is provided. In particular, the invention permits observation of cell culture (or other biological medium) at physiological conditions. The temperature can be held constant and the sample chamber humidified. The small volume of the sample chamber allows for rapid attainment of desired atmospheric conditions. The apparatus consists of a miniature incubator suitable for the placing of a standard petri-dish or culture dish, a hollow fibre purging tube sandwiched between two porous water saturated pads provides humidified gas to the chamber, which gas escapes through the observation hole in the base of the incubator. Heating means provided to the incubator consists of e.g. a warm water jacket in intimate contact with the external wall of the incubator. A temperature sensing means, such as a thermocouple, is provided in the interior of the incubator.

U.S. Pat. No. 4,707,086 relates to an assembly which can provide a wide range of temperatures and pressures to the sample cell of an optical microscope to facilitate transient thermodynamic studies. The assembly consists of a sample chamber containing optical windows, said chamber having protruding into it means for fixing and/or monitoring the temperature and pressure within the chamber. The chamber is located within an outer envelope within which is provided means for heating and cooling the chamber. The apparatus is particularly applicable to the study of behaviour of crystalline materials placed under pressure in field of geology or study of fluids. More generally, it is applicable to studies of the effects of pressure and temperature variations in solid state physics, chemistry and biology.

U.S. Pat. No. 5,257,128 relates to a microscope stage assembly providing control of thermal and fluid environment of samples whilst under simultaneous observation. The apparatus allows continuous observation and movement/rotation of the sample. The apparatus comprises a sample chamber with an inlet and outlet for fluid supplied from a reservoir for controlling the fluid environment, a temperature control means for regulating the temperature in the range −100° C. to 100° C. and optical windows for microscopic observation of the sample. This apparatus has particular application to studies of cryopreservation of cells and other biological materials.

U.S. Pat. No. 4,336,329 relates to apparatus for use in the treatment of biological materials, particularly cultivation of biological materials (i.e. a type of incubator) and to a method of using such apparatus. The atmosphere may be controlled such that the incubator approximates different conditions in vivo. The apparatus comprises a cultivating space fed by a gas (air, oxygen, nitrogen and/or carbon dioxide) inlet and a second inlet for steam. The gas streams enter the incubating chamber via a bypass duct, which may temporarily be closed off from the main incubating space to allow mixing of the two streams. The cultivating space may be sealed off and heated and cooled as desired.

DE 9414990 U relates to an air conditioning module in which water is sprayed into an air stream to create a humidified air stream. The humidified air stream can then be mixed with a main air stream, which passes a heating element and is then blown from a ventilating zone into the space in which effective climate control is required.

WO 00/25129 relates to apparatus and a method for inverse gas chromatography. The method includes, for example, the use of a carrier fluid of known vapour content, wherein the vapour is a probe material for use in the chromatographic separation.

Although, some of the prior art systems have limited control of the environment in terms of temperature or pressure of the sample chamber, or enable the maintenance of high humidity for the study of cell cultures, there is no provision for accurate control of temperature and gaseous composition within a sample chamber of an analytical device.

The present invention provides apparatus for examining a sample by microscopy, spectroscopy or crystallography in a controlled environment comprising a vapour of a volatile substance, wherein the apparatus comprises a sample chamber, means for controlling the temperature of the sample chamber, a gas inlet to the sample chamber and a gas outlet from the sample chamber, means for generating a first gas stream substantially free of the volatile substance, means for generating a second gas stream substantially saturated by the volatile substance, means for mixing the first and second gas streams in a controlled ratio to generate a third gas stream having a desired content of the volatile substance and means for passing the third gas stream to the gas inlet of the sample chamber, to provide the controlled environment having the said desired content of the volatile substance.

Preferably, there is also provided means for maintaining the apparatus, and particularly, at least the sample chamber, the third gas stream, the means for mixing the first and second gas streams and the second gas stream at substantially the same temperature.

The invention further provides a sample block for examining a sample by microscopy, spectroscopy or crystallography in a controlled environment comprising a vapour of a volatile substance, wherein the sample block comprises a sample chamber, a gas inlet to the sample chamber and a gas outlet from the sample chamber, a conduit for containing a first gas stream substantially free of the volatile substance, a chamber for containing a liquid reservoir of the volatile substance, the chamber defines a vapour space above the liquid reservoir, an outlet from the vapour space of the reservoir for passage of a second gas stream substantially saturated by the volatile substance, means for mixing the first and second gas streams to generate a third gas stream and means for feeding the third gas stream to the gas inlet to the sample chamber.

The means for controlling the temperature of the sample chamber may comprise a temperature controller, a peltier heat pump and a fluid circulation pump.

It is a preferred feature of the invention that the temperature of the sample chamber can be controlled to within 0.5° C. and more preferably to within 0.1° C. It is also preferable that the apparatus and particularly the sample chamber, the second gas stream, the means for mixing the first and second gas streams and optionally at least a portion of the first gas stream and the means for generating the second gas stream may be maintained at the same temperature to +/−0.5° C., and more preferably to +/−0.1° C.

It is also preferred that the mixing means for generating a third gas stream is such as to enable control of the relative vapour pressure of the volatile substance in the third gas stream to within 2.5% and more preferably to within 1% of a desired relative vapour pressure.

The volatile substance is preferably water, but may be an organic liquid. The first gas stream is preferably a gas which is generally used, such as dry air, nitrogen, argon or helium.

In one embodiment, the first gas stream is air, the volatile substance is water and the second gas stream is air saturated with water vapour. The third gas stream is air with a desired proportion of water vapour, from 0% to 100% humidity.

The concentration of volatile substance in the third gas stream and provided to the sample chamber is controlled by the relative supplies of the first gas stream and the source gas provided to the reservoir.

In a particularly preferred embodiment, the sample chamber is located within a thermally conducting sample block. Such a thermal conducting sample block may be a monolithic block of metal e.g. aluminium, brass or stainless steel.

The second gas stream may be generated within the sample block by means of passing a source gas through a reservoir of the volatile substance, which is located in a chamber within the sample block for containing said reservoir of the volatile substance, to generate a gas substantially saturated by the volatile substance, said gas exiting said chamber through an outlet from the gas space of the reservoir. The invention may provide a means, located within the sample block, for feeding the second gas stream to the mixing means. Optionally, the flowpath for the second gas stream is contained entirely within the sample block.

The apparatus of the invention may optionally further comprise a sensor for measuring the vapour content of the atmosphere. The sensor may be e.g. a relative humidity sensor.

The apparatus may optionally contain windows above and below the sample chamber to allow e.g. observation, transmission of radiation and/or illumination of the sample. The windows are preferably double or triple glazed to prevent heat loss from the sample chamber and condensation of the volatile substance from the atmosphere and may be transparent to the type of radiation being used to prove the sample e.g. in the case of spectroscopy and X-ray diffraction and may be chemically resistant to vapours of the volatile substance.

The apparatus of the present invention may further comprise a control module, said control module comprising at least a means for regulating temperature and a means for regulating gas flow and optionally a power supply. The apparatus may further be integrated with a suitably programmed computer.

The apparatus of the present invention may interface with an analytical device, such as a microscope, a photon spectroscopic device or an X-ray diffractometer. The apparatus of the present invention may therefore be used to study physical and chemical changes in a solid or liquid sample due to the amount of vapour (or humidity) surrounding the sample at a particular temperature.

The microscope may be, for example, an infra-red microscope or, preferably, an optical microscope.

A preferred embodiment of the invention will now be described with reference to the accompanying drawings. In the drawings:—

Figure 1:
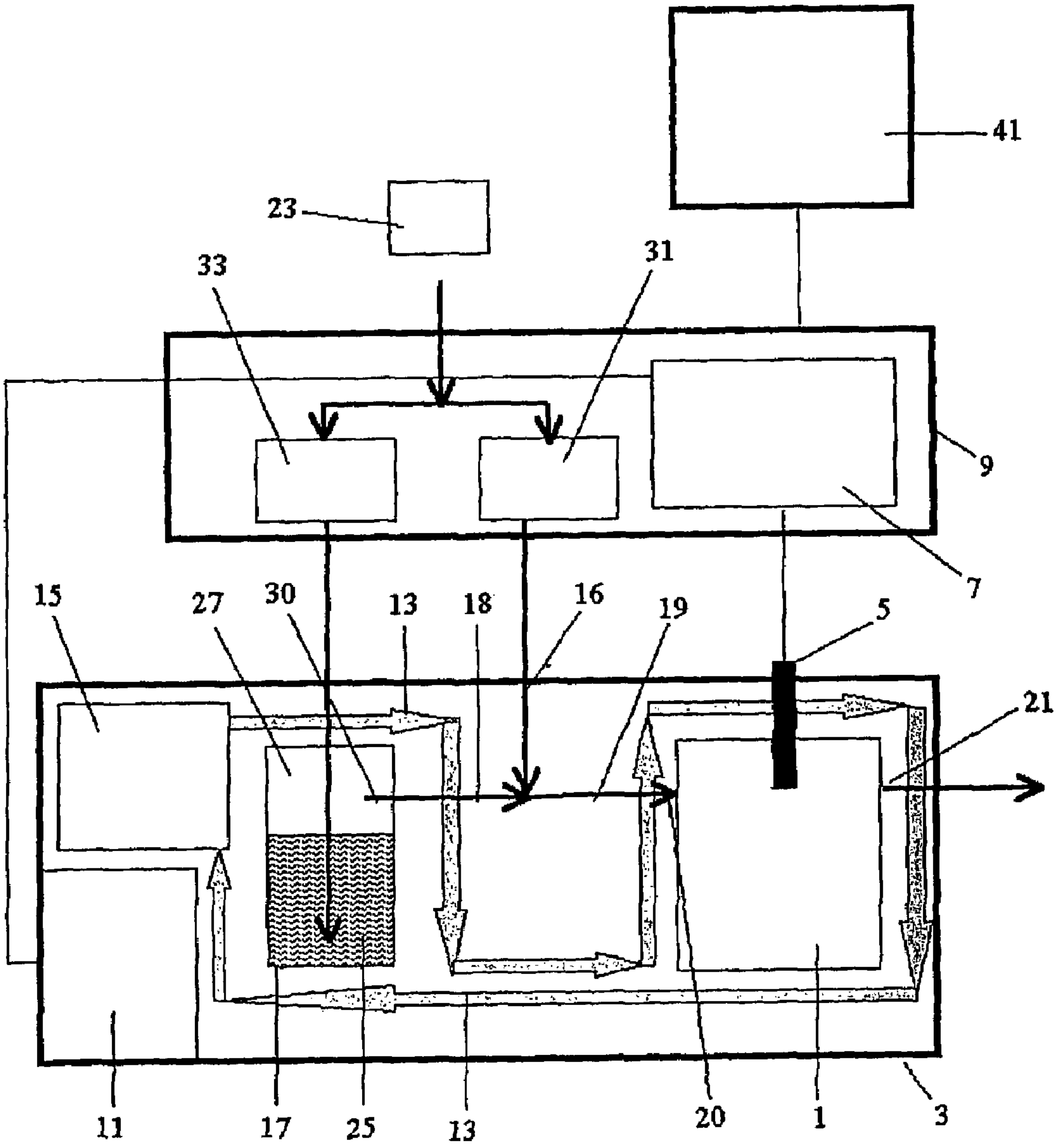
FIG. 1 shows a schematic representation of the system in combination with a control module and computer.
Figure 2:
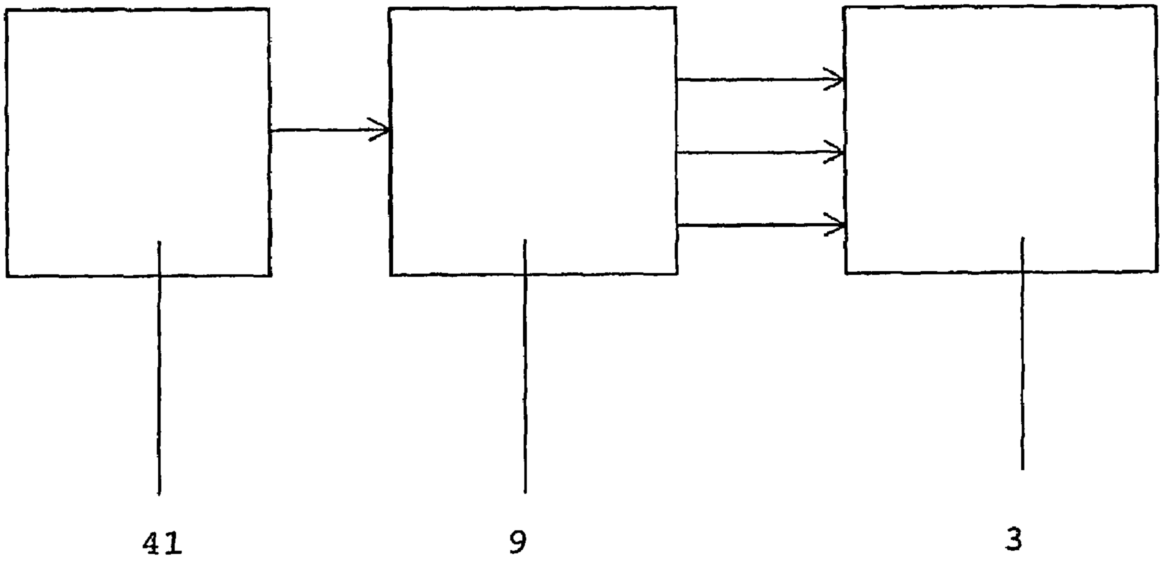
FIG. 2 shows of a schematic of the relationship of the system when integrated with a control module and a computer.

With reference to FIG. 1, the apparatus of the present invention comprises a sample chamber (1) located within a sample block (3), a means for regulating the temperature of the sample chamber (1) comprising a temperature sensor (5), integral with the sample block (3) and sample chamber (1), and a temperature controller (7) located within a control module (9). The sample block (3) is heated and cooled by means of a Peltier heat pump (11) and an even distribution of temperature throughout the sample block (3) is provided by a continuous fluid circulation channel (13) and a fluid circulation pump (15), all located within sample block (3).

The fluid in continuous fluid circulation channel (13) may be, for example, water or silicone oil. The fluid circulation pump (15) may recirculate the fluid several times per minute to ensure a fast response and an even temperature distribution throughout sample block (3).

A first gas stream (16), substantially free of a volatile substance contained in reservoir chamber (17), is mixed with a second gas stream (18), substantially saturated with the volatile substance, in a controlled ratio to form a third gas stream (19).

Sample chamber (1) is fed with a third gas stream (19) through an inlet (20) to the sample chamber and is vented through an outlet (21).

The second gas stream (18) is generated by feeding a controlled flow of gas from a gas source (23) through a liquid reservoir (25) of the volatile substance located in the reservoir chamber (17) within sample block (3). The vapour space (27) of reservoir (25) contains a gas saturated with the volatile substance which provides the second gas stream (18) by escaping through an outlet from the vapour space (30).

The ratio of the first (16) and second (18) gas streams present in the third gas stream (19) is controlled by Mass Flow Controllers (31) and (33) for controlling the mass flow of source gas providing the first (16) and second (18) gas streams respectively. The mass flow controllers (31 & 33) are located in the control module (9) and fed from a gas source (23).

A computer (41) may be connected to the control module (9) for automated temperature and gas composition of the apparatus. The concentration of the volatile substance in third gas stream (19) is defined by the proportions of the first gas stream (16) and second gas stream (18) and the temperature of the sample block (3).

The invention claimed is:

1. Apparatus for examining a sample by microscopy, spectroscopy or crystallography in a controlled environment comprising a vapour of a volatile substance, wherein the apparatus comprises:

a sample chamber;

means for controlling the temperature of the sample chamber;

a gas inlet to the sample chamber and a gas outlet from the sample chamber;

means for generating a first gas stream substantially free of the volatile substance;

means for generating a second gas stream substantially saturated by the volatile substance;

means for mixing the first and second gas streams in a controlled ratio to generate a third gas stream having a desired content of the volatile substance;

and means for passing the third gas stream to the gas inlet of the sample chamber, to provide the controlled environment having the said desired content of the volatile substance.

2. Apparatus as claimed in claim 1, which further comprises means for maintaining:

the sample chamber, the third gas stream, the means for mixing the first and second gas streams, and the second gas stream, at substantially the same temperature.

3. Apparatus as claimed in claim 2, wherein the temperature maintaining means is such as to maintain the said temperature to within +/−0.1° C. of a desired temperature.

4. Apparatus as claimed in claim 1, for examining a sample by microscopy, which further comprises an optical microscope.

5. Apparatus as claimed in claim 1, wherein the volatile substance is water.

6. Apparatus as claimed in claim 1, wherein the first gas stream is dry air.

7. Apparatus as claimed in claim 1, wherein the second gas stream is humidified air.

8. Apparatus as claimed in claim 1, wherein the sample chamber is located within a thermally conducting sample block.

9. Apparatus as claimed in claim 8 wherein the mixing means is located in the thermally conducting sample block.

10. Apparatus as claimed in claims 8 or 9 wherein the means for generating a second gas stream comprises:

a chamber located in the sample block for containing a reservoir of the volatile substance; and means for passing a gas flow through the liquid reservoir in the chamber to provide the second gas stream substantially saturated by the volatile substance.

11. Apparatus as claimed in claims 8 or 9, wherein the second gas stream is contained entirely within the sample block.

12. Apparatus as claimed in claim 1, further comprising a sensor for measuring the content of the volatile substance in the third gas stream.

13. Apparatus as claimed in claim 1, wherein the sample chamber further comprises a viewing window for the said examination.

14. Apparatus as claimed in claim 1, further comprising a control module, said control module comprising:

means for regulating temperature; and means for regulating gas flow.

15. Apparatus as claimed in claim 10, wherein the second gas stream is contained entirely within the sample block.

16. Apparatus as claimed in claim 14, further comprising a computer suitably programmed to operate with the apparatus.

17. A sample block for examining a sample by microscopy, spectroscopy or crystallography in a controlled environment comprising a vapour of a volatile substance, wherein the sample block comprises:

a sample chamber;

a gas inlet to the sample chamber and a gas outlet from the sample chamber;

a conduit for containing a first gas stream substantially free of the volatile substance;

a chamber for containing a liquid reservoir of the volatile substance, the chamber defines a vapour space above the liquid reservoir;

an outlet from the vapour space of the reservoir for passage of a second gas stream substantially saturated by the volatile substance; means for mixing the first and second gas streams to generate a third gas stream; and means for feeding the third gas stream to the gas inlet to the sample chamber.

18. A sample block as claimed in claim 16, which includes means for feeding a gas through the liquid reservoir to form the second gas stream.

19. A sample block as claimed in claim 16, further comprising a sensor for measuring the composition of the third gas stream.

20. Apparatus for examining a sample by microscopy, spectroscopy or crystallography in a controlled environment comprising a vapour of a volatile substance, wherein the apparatus comprises:

a sample chamber;

a temperature controller for controlling the temperature of the sample chamber;

a gas inlet to the sample chamber and a gas outlet from the sample chamber;

a gas stream generator that generates a first gas stream substantially free of the volatile substance;

a gas stream generator that generates a second gas stream substantially saturated by the volatile substance;

a gas mixer that mixes the first and second gas streams in a controlled ratio to generate a third gas stream having a desired content of the volatile substance;

said third gas stream being directed to the gas inlet of the sample chamber to provide the controlled environment having the said desired content of the volatile substance.

* * * * *

UNITED STATES PATENT AND TRADEMARK OFFICE

CERTIFICATE OF CORRECTION

PATENT NO. : 7,160,718 B2
APPLICATION NO. : 10/296720
DATED : January 9, 2007
INVENTOR(S) : Carl Levoguer et al.

It is certified that error appears in the above-identified patent and that said Letters Patent is hereby corrected as shown below:

*Please add the following to the title page of the issued patent:

Item -- (30) Foreign Application Priority Data
May 31, 2000 (GB).......................................0013261.3 --

Signed and Sealed this

Seventeenth Day of July, 2007

JON W. DUDAS
*Director of the United States Patent and Trademark Office*